(12) United States Patent
Imada et al.

(10) Patent No.: US 9,036,893 B2
(45) Date of Patent: May 19, 2015

(54) TIRE DEFECT DETECTION METHOD

(75) Inventors: Munetoshi Imada, Osaka (JP);
Hirokatsu Mizukusa, Osaka (JP);
Toshihiko Iwatani, Osaka (JP);
Hiroyasu Koshimizu, Nagoya (JP);
Takayuki Fujiwara, Ebetsu (JP)

(73) Assignees: Sharp Kabushiki Kaisha, Osaka (JP);
Toyo Tire & Rubber Co., Ltd., Osaka (JP)

( * ) Notice: Subject to any disclaimer, the term of this patent is extended or adjusted under 35 U.S.C. 154(b) by 0 days.

(21) Appl. No.: 14/117,893

(22) PCT Filed: May 17, 2012

(86) PCT No.: PCT/JP2012/062693
§ 371 (c)(1),
(2), (4) Date: Nov. 22, 2013

(87) PCT Pub. No.: WO2012/157716
PCT Pub. Date: Nov. 22, 2012

(65) Prior Publication Data
US 2014/0086453 A1 Mar. 27, 2014

(30) Foreign Application Priority Data
May 17, 2011 (JP) .................. 2011-110874

(51) Int. Cl.
*G06K 9/00* (2006.01)
*G01B 11/30* (2006.01)
(Continued)

(52) U.S. Cl.
CPC ............ *G06K 9/00791* (2013.01); *G01B 11/30* (2013.01); *G01N 21/95* (2013.01); *G01N 21/952* (2013.01); *G01M 17/027* (2013.01);
*G06T 5/005* (2013.01); *G06T 7/0008* (2013.01); *G06T 2207/20021* (2013.01);
(Continued)

(58) Field of Classification Search
None
See application file for complete search history.

(56) References Cited

U.S. PATENT DOCUMENTS 7,755,772 B2 * 7/2010 Takahashi et al. ............ 356/601
8,218,153 B2 * 7/2012 Kostka et al. ................. 356/603
(Continued)

FOREIGN PATENT DOCUMENTS

CN 101363724 A 2/2009
JP 05-187843 A 7/1993
(Continued)

OTHER PUBLICATIONS

Official Communication issued in corresponding International Application PCT/JP2012/062693, mailed on Nov. 28, 2013.
(Continued)

Primary Examiner — Anand Bhatnagar
Assistant Examiner — Soo Park
(74) Attorney, Agent, or Firm — Keating & Bennett, LLP

(57) ABSTRACT

Provided is a tire defect detection method capable of accurately detecting a thinly extending convex defect of a tire surface. Prior to the start of Step S1, two-dimensional images including a slit light image are successively obtained in advance. In Step S1, a slit light image is extracted from data of a plurality of shot two-dimensional images. In Step S2, an eccentricity component which is deviation resulting from eccentricity is eliminated from the extracted slit light image. In Step S3, a feature quantity is calculated based on the light image from which the eccentricity component is eliminated, and in Step S4, a thinly extending convex defect is detected based on the calculated feature quantity.

4 Claims, 8 Drawing Sheets

(51) Int. Cl.
  *G01N 21/95* (2006.01)
  *G01N 21/952* (2006.01)
  *G01M 17/02* (2006.01)
  *G06T 5/00* (2006.01)
  *G06T 7/00* (2006.01)

(52) U.S. Cl.
  CPC ........... *G06T 2207/20056* (2013.01); *G06T 2207/20061* (2013.01); *G06T 2207/20201* (2013.01)

(56) References Cited

U.S. PATENT DOCUMENTS

| | | |
|---|---|---|
| 2001/0024279 A1 | 9/2001 | Kaneko et al. |
| 2005/0058333 A1 | 3/2005 | Kaneko et al. |
| 2009/0040533 A1 | 2/2009 | Takahashi et al. |
| 2011/0188731 A1* | 8/2011 | Sekiguchi ............... 382/141 |
| 2011/0288814 A1 | 11/2011 | Mizutani et al. |

FOREIGN PATENT DOCUMENTS

| | | | |
|---|---|---|---|
| JP | 10-160452 A | | 6/1998 |
| JP | 2001-249012 A | | 9/2001 |
| JP | 2003-240521 A | | 8/2003 |
| JP | 2008-185511 A | | 8/2008 |
| JP | 2008185511 A | * | 8/2008 |
| JP | 2011-247646 A | | 12/2011 |

OTHER PUBLICATIONS

Official Communication issued in International Patent Application No. PCT/JP2012/062693, mailed on Aug. 7, 2012.

* cited by examiner

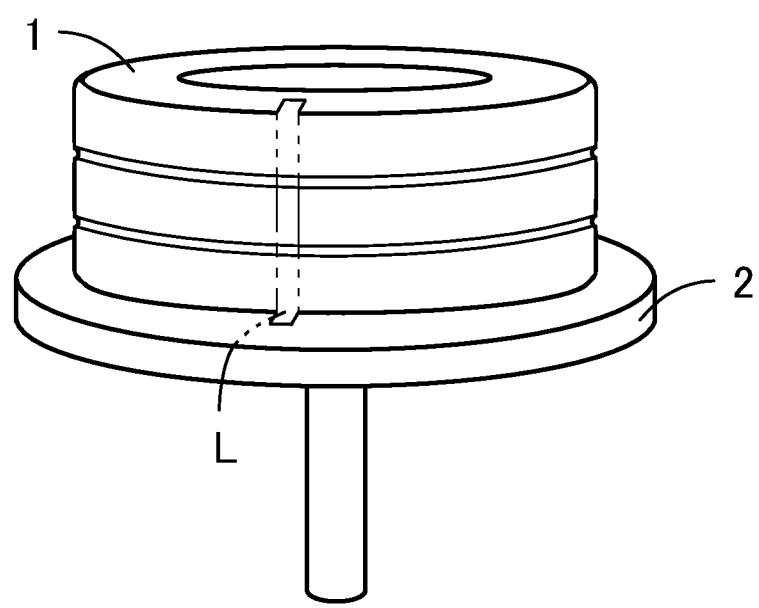

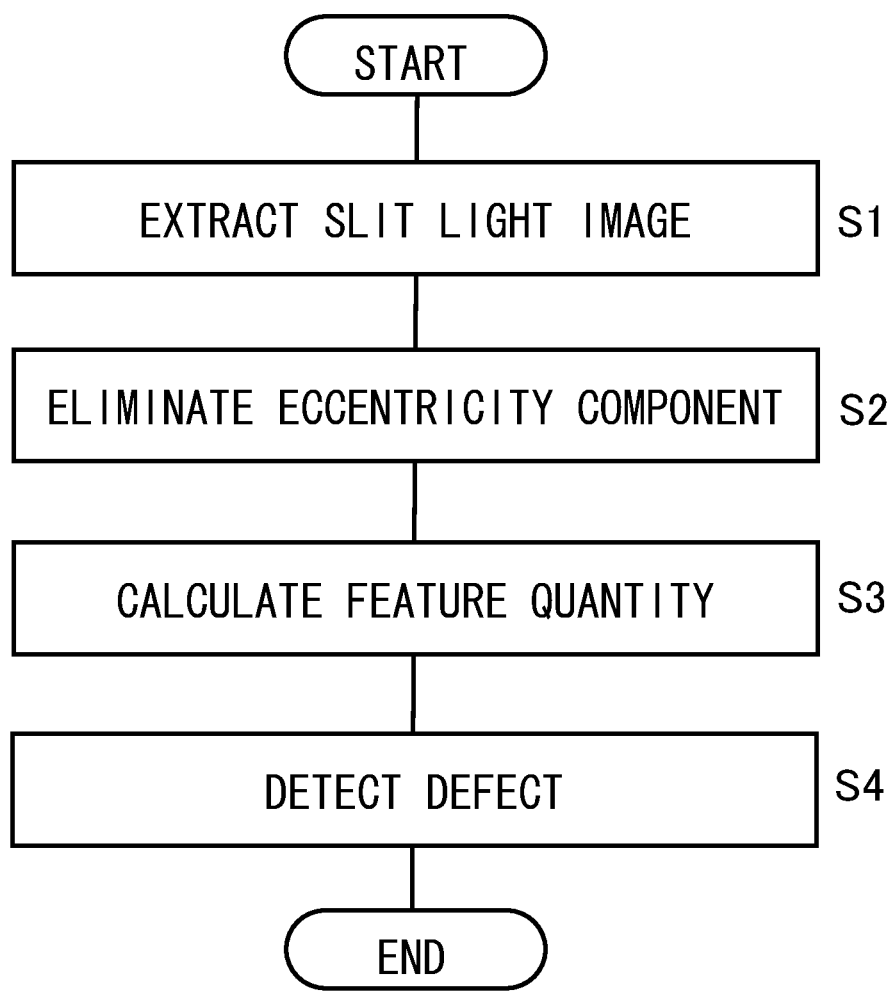

TIRE DEFECT DETECTION METHOD

TECHNICAL FIELD

The present invention relates to a tire defect detection method for detecting a defect of a tire surface.

BACKGROUND ART

In defect inspection of a tire surface, a method of inspecting a defect based on a slit light image obtained by irradiation with slit light is used.

An inspection method described in Patent Literature 1 is for performing quality judgment of appearance and shape of a tire based on appearance data by a line sensor of a linear portion irradiated with first slit light on a tire surface and shape data by an area sensor of the same linear portion lighted by second slit light.

Moreover, an inspection method described in Patent Literature 2 is for performing quality judgment of appearance and shape based on density (or color) and position information obtained by shooting an irradiated portion of slit light by an area sensor while rotating a tire.

CITATION LIST

Patent Literature

Patent Literature 1: Japanese Unexamined Patent Publication JP-A 2001-249012
Patent Literature 2: Japanese Unexamined Patent Publication JP-A 2003-240521

SUMMARY OF INVENTION

Technical Problem

As a defect of a tire surface, there is a defect which is a thinly extending convex (hereinafter, referred to as "thinly extending convex defect"). This defect is difficult to be found with naked eyes, and inspection by a slit light image as described in Patent Literatures 1 and 2 is necessary.

Moreover, in order to efficiently inspect the entire surface, it is desired to perform inspection by successively obtaining slit light images while rotating a tire about a rotation axis.

In the inspection method described in Patent Literature 1, the slit light image is obtained by both of the line sensor and an area camera, and it is difficult to adjust a position relation therebetween or the like. Further, it is not considered to perform inspection successively while rotating the tire.

In the case of performing inspection while rotating the tire, deviation is generated in the slit light image to be shot. This deviation is caused because outer shape itself of the tire is not a complete circle and eccentricity is caused that the center of rotation of the tire is not coincident with the center of rotation of a rotational table which rotates the tire, which causes deviation in a radial direction of the tire and makes detection of the thinly extending convex defect more difficult.

The inspection method described in Patent Literature 2 is a method of performing inspection while rotating the tire, but such deviation at the time of shooting is not considered, so that it is not possible to detect the thinly extending convex defect accurately.

An object of the invention is to provide a tire defect detection method capable of accurately detecting a thinly extending convex defect of a tire surface.

Solution to Problem

The invention provides a tire defect detection method for detecting a convex defect in a contact area of a tire comprising tread pattern elements, comprising:
a shooting step of successively shooting two-dimensional images of an area of the tire including a region irradiated with slit light by irradiating a tire tread with the slit light so that a longitudinal direction thereof becomes parallel to a width direction of the tire, while rotating the tire about a predetermined axis;
an extraction step of removing, from among light images of the slit light appearing in respective shot two-dimensional images, a light image other than linear light images which are light images of the contact area of the tire and extracting the linear light images;
an eliminating step of eliminating an influence of displacement of the contact area resulting from the rotation of the tire, from the two-dimensional images including the extracted linear light images;
a calculation step of calculating a difference between a position of the linear light image in each of the two-dimensional images from which the influence of displacement is eliminated and an average position of linear light images in all two-dimensional images from which the influence of displacement is eliminated as a feature quantity for each of the two-dimensional images; and
a detection step of comparing a calculated feature quantity for each of the two-dimensional images and a predetermined threshold, and in a case where the feature quantity is larger than the predetermined threshold, determining that the tire has some defect.

Moreover, in the invention, it is preferable that in the eliminating step, a position of center of gravity of the extracted linear light image is calculated for each of the two-dimensional images including the extracted linear light image, Fourier transform is performed for a change between calculated positions of center of gravity as waveform data, inverse Fourier transform is performed for a frequency spectrum which is obtained by eliminating a high-frequency component from the frequency spectrum obtained by Fourier transform, a position of center of gravity after transform that is a position of center of gravity after inverse Fourier transform is obtained, and a difference between the position of center of gravity and the position of center of gravity after transform is defined as an influence of displacement of the contact area.

Moreover, in the invention, it is preferable that in the calculation step, the two-dimensional image from which the influence of displacement is eliminated is divided into a plurality of blocks in parallel to a circumferential direction of the tire and a feature quantity for respective divided blocks is calculated.

Advantageous Effects of Invention

According to the invention, in a shooting step, two-dimensional images of an area of a tire including a region irradiated with slit light are successively shot by irradiating a tire tread with the slit light so that a longitudinal direction thereof becomes parallel to a width direction of the tire, while rotating the tire about a predetermined axis. In an extraction step, from among light images of the slit light appearing in respective shot two-dimensional images, a light image other than linear light images which are light images of a contact area of tire is removed and the linear light images are extracted.

In an eliminating step, an influence of displacement of the contact area resulting from the rotation of the tire is eliminated from the two-dimensional images including the extracted linear light images, and in a calculation step, a difference between a position of the linear light image for each of the two-dimensional images including the linear light image from which the influence of displacement is eliminated and an average position of linear light images in all two-dimensional images is calculated as a feature quantity for each of the two-dimensional images.

In a detection step, a calculated feature quantity for each of the two-dimensional images and a predetermined threshold are compared, and in a case where when the feature quantity is larger than the predetermined threshold, it is determined that the tire has some defect.

Thereby, just by shooting a light image of slit light by an area camera, it is possible to detect a defect with a simple structure. Moreover, the influence of displacement of the contact area by rotation is eliminated by the eliminating step, it is possible to accurately detect a defect of the tire surface.

According to the invention, in the eliminating step, a position of center of gravity of the extracted linear light image is calculated for each of the two-dimensional images, and Fourier transform is performed for displacement of the calculated position of center of gravity as waveform data. Inverse Fourier transform is performed for a frequency spectrum which is obtained by eliminating a high-frequency component from the frequency spectrum obtained by Fourier transform, and a position of center of gravity after transform that is a position of center of gravity after inverse Fourier transform is obtained. A difference between the position of center of gravity and the position of center of gravity after transform is defined as an influence of displacement of the contact area. For example, by shifting the position of the linear light image by this difference, it is possible to eliminate the influence of displacement of the contact area.

According to the invention, in the calculation step, the two-dimensional image is divided into a plurality of blocks in parallel to a circumferential direction of the tire and a feature quantity for respective divided blocks is calculated. Since the block shows a position of a width direction of the tire, it is possible to easily detect an actual position of a defect of the tire surface based on the block in which the defect is detected.

BRIEF DESCRIPTION OF DRAWINGS

Other and further objects, features, and advantages of the invention will be more explicit from the following detailed description taken with reference to the drawings wherein:

FIG. 1A is a schematic perspective view showing a state where a slit light image of a tire surface is shot;

FIG. 2 is a flowchart showing a defect detection method according to an embodiment of the invention;

DESCRIPTION OF EMBODIMENTS

Description will hereinafter be given in detail for preferred embodiments of the invention with reference to drawings.

FIG. 1A is a schematic perspective view showing a state where a slit light image of a tire surface is shot. As shown in FIG. 1A, a tire 1 to be inspected is placed on a rotational table 2, and a tire surface is irradiated with slit light L while rotating the rotational table 2 about an axis thereof. Irradiation of the slit light is performed so that a longitudinal direction thereof is parallel to a width direction of the tire. On a surface of a tread of the tire 1, grooves are provided along a circumferential direction (tread pattern elements), and the slit light image is composed of light images of mainly three regions of a contact area of the tread, an inner wall surface and a bottom surface of the groove section.

Figure 1B:
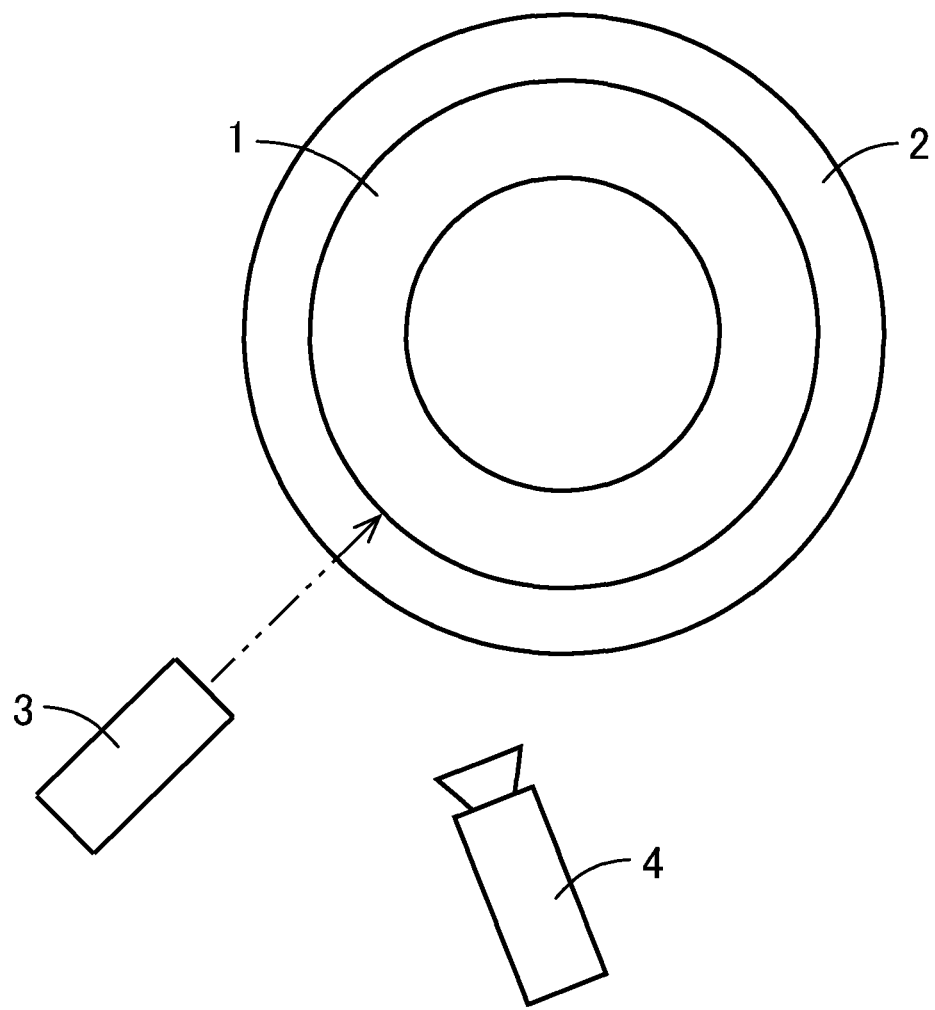
FIG. 1B is a schematic plan view showing a state where the slit light image of the tire surface is shot.

FIG. 1B is a schematic plan view showing a state where the slit light image of the tire surface is shot. As shown in FIG. 1B, the contact area of the tread of the tire 1 is irradiated with the slit light L from a slit light source 3, and a predetermined region including a region irradiated with the slit light is shot by an area camera 4 to obtain two-dimensional image data. At this time, the tire 1 rotates about a rotation axis by the rotational table 2, and the area camera 4 can successively obtain slit light images of the surface of the tire 1.

In the present embodiment, the slit light L is laser light, and, for example, red laser with a wavelength of around 650 nm, green laser with a wavelength of around 530 nm, or the like are usable. As a light source of the laser light, for example, a laser head manufactured by NEOARK Corporation (DMSH-6505L, wavelength 650 nm, output power 3 mW) or the like are usable. Note that, irradiation of one or plural sets of the slit light L may be performed, and in the case of irradiation of plural sets of the slit light, slit light images to be obtained becomes plural as well. Though each step describe below is explained for a case where irradiation of one set of slit light is performed, similar processing may be performed for each slit light image in the case of irradiation of plural sets of the slit light.

Note that, two-dimensional image data from which a slit light image is to be extracted is shot, for example, by shutting out outside light to the tire surface. As a method for shutting out outside light, light sources other than the slit light source 3 in a room where shooting is performed, for example, such as interior light, are all turned off. Shooting is preferably performed in a windowless room. When a window is provided, outside light is shut out by blackout curtains, shading curtains, blinds or the like. In addition, the tire 1, the rotational table 2, the slit light source 3 and the area camera 4 may be all covered with a dark box. Further, shooting may be performed in a state where a filter which does not transmit light other than slit light is mounted on a lens of the area camera 4. For example, a red filter manufactured by VS Technology Corporation (SV-R60-270) or the like are usable.

When a thinly extending convex defect exists on the contact area of the tread of the tire 1, slit light image by irradiation of the slit light L to a convex portion is obtained as an image along with a surface shape of the convex portion, so that if such an image due to the thinly extending convex defect (defect image) can be detected among slit light images, the thinly extending convex defect can be detected.

Here, though the thinly extending convex defect is a defect and therefore has various sizes and shapes, the defect to be detected is a convex portion which has an approximate area of 100 mm$^2$ or more and height from the contact area of the tread of 0.3 mm or more.

Since the defect image appears at a position deviating from the linear light image which is a light image of the contact area of the tread, the defect defining a deviation quantity from the linear light image as a feature quantity is detected.

In the schematic procedure of the embodiment of the invention, after whole circumference of the tire surface is measured, the result of projecting the slit light image is firstly extracted in each frame of the two-dimensional image which is shot. An average value of the abscissa (hereinafter, X-coordinate) is obtained as a representative position of the slit light image in each extracted frame. Though the average value of the X-coordinate is displaced from side to side as the frame advances, this displacement results from eccentric rotation of the tire, so that an eccentricity component is eliminated based on a displacement quantity. For an image from which the eccentricity component is eliminated, the feature quantity is obtained to detect a defect. FIG. 2 is a flowchart showing a defect detection method according to an embodiment of the invention.

Prior to the start of Step S1, two-dimensional images including a slit light image are successively obtained in advance by a method as shown in FIG. 1.

In Step S1, a slit light image is extracted from data of a plurality of shot two-dimensional images. In Step S2, an eccentricity component which is deviation resulting from eccentricity is eliminated from the extracted slit light image. In Step S3, a feature quantity is calculated based on the light image from which the eccentricity component is eliminated, and in Step S4, a thinly extending convex defect is detected based on the calculated feature quantity.

Description will be given in detail below for each of these steps.

<Step S1> Extraction of Slit Light Image

Figure 3:
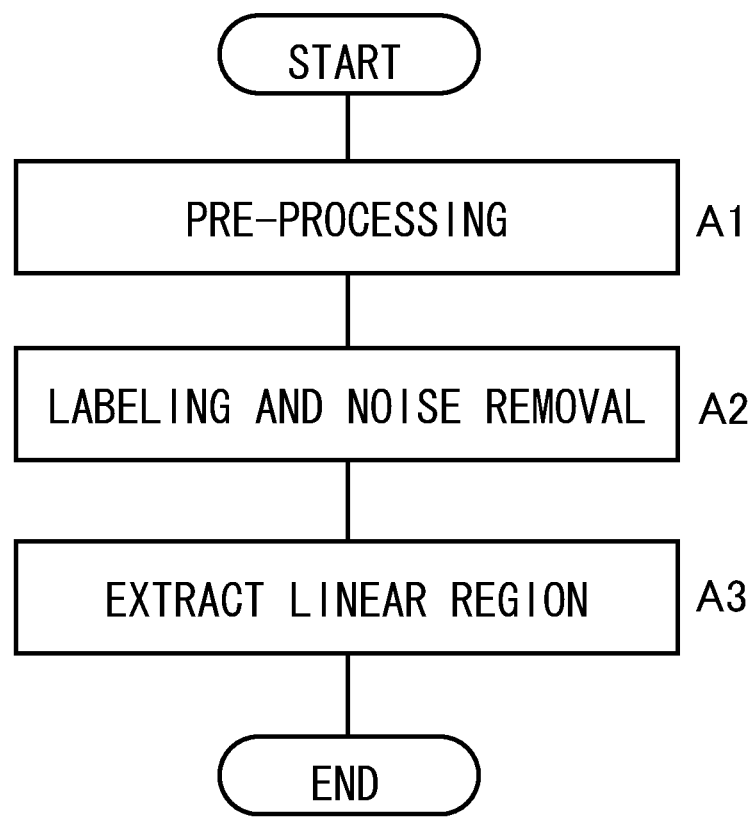
FIG. 3 is a flowchart showing procedure for extracting the slit light image.

In the extraction of the slit light image, for detecting a defect image, an image other than the linear light image, that is, a light image due to the groove provided in the tread or the like is removed from the slit light image to extract only the linear light image. FIG. 3 is a flowchart showing procedure for extracting the slit light image.

Figure 4:
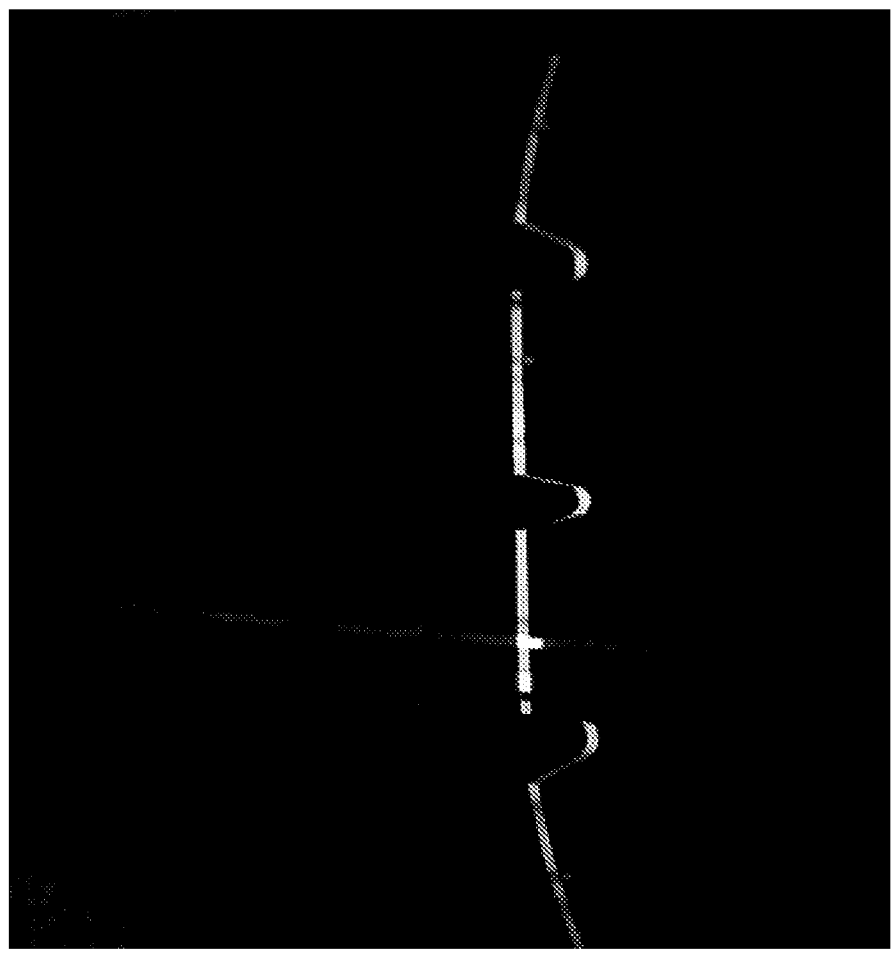
FIG. 4 is a view showing an example of a two-dimensional image shot by an area camera.

Note that, a size of the slit light is 200 mm length and 3 mm width in this embodiment. FIG. 4 is a view showing an example of a two-dimensional image shot by the area camera 4. Only a portion irradiated with the slit light is shot as a light image and other portion does not appear in the image. In addition, three curved portions are by the groove of the tread pattern, and thickly appearing portions are portions reflected by a color line drawn on the contact area of the tread.

Only the slit light image projected on the contact area is extracted by removing the light image by the groove, the light image by reflection and the like.

As shown in FIG. 3, pre-processing is performed at Step A1, labeling and noise removal of the light image are performed at Step A2 to extract only a linear region of the slit light image.

[Step A1] Pre-Processing

As the pre-processing, the shot two-dimensional image data is binarized, and is further subjected to expansion processing and contraction processing. A threshold at the time of binarization can be determined by a publicly known method, but a discrimination analysis method is used in this embodiment. After the expansion processing is performed m-times for the binarized image data, the contraction processing is performed m-times. For example, m=3. Here, by performing the expansion processing previously, it is possible, even when the shot slit light image has a cut, to eliminate the cut.

Figure 5:
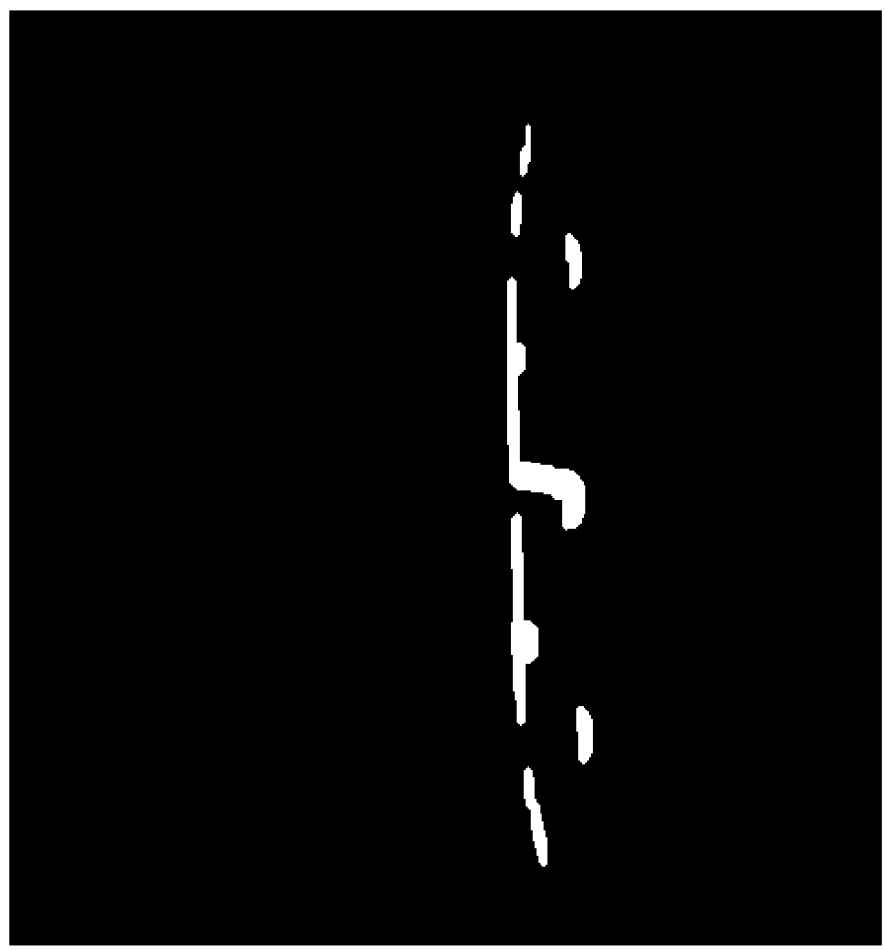
FIG. 5 is a view showing an image after pre-processing.

FIG. 5 is a view showing an image after the pre-processing. The slit light image of the contact area and the slit light image other than of the contact area are isolated in conjunction or in parallel. In addition, a portion of the light image that becomes thick by reflection has a small luminance value as the light image because light quantity is essentially small and can be almost removed by binarization processing, but one near the slit light has a high luminance value and is therefore becomes thick, and cannot be removed even by the pre-processing.

The pre-processing as described above is processing which is performed for one frame, and the pre-processing is performed for all shot frames.

[Step A2] Labeling and Noise Removal

For a portion of the slit light image that becomes thick by reflection and a portion where the slit light images of the inner wall surface and the bottom surface of the groove are connected, a thickness of the light image in that region is calculated. Labeling processing is applied to the whole image, projection processing is performed in an X direction in each label, and central values Pn are calculated from projection images of all labels. Here, n is a frame number, and projection processing and calculation of the central value are performed for each one frame.

First, a threshold $th_{n,d}$ is determined based on the following formula (1). Threshold processing is performed for each row of the projection image using the threshold $th_{n,d}$, and the row with the threshold $th_{n,d}$ or more is removed. This processing makes it possible to delete a row which has a thickness with the threshold $th_{n,d}$ or more and to remove the portion which becomes thick by connection such as light images of the groove.

Subsequently, a threshold $th_{n,s}$ is determined based on the following formula (2). In the row with the threshold $th_{n,s}$ or more among rows with the threshold $th_{n,d}$ or less, replacement is performed with the same value as $th_{n,s}$. This makes is possible to narrow the portion which is not as thick as the connection portion but becomes slightly thick by reflection.

[Math. 1]

$$th_{n,d} = P_n \times C_d \quad (1)$$

$$th_{n,s} = P_n \times X_S \quad (2)$$

Here, $C_d$ and $C_s$ are predetermined coefficients. For example, $C_d$=2.5 and $C_s$=1.2.

Figure 6:
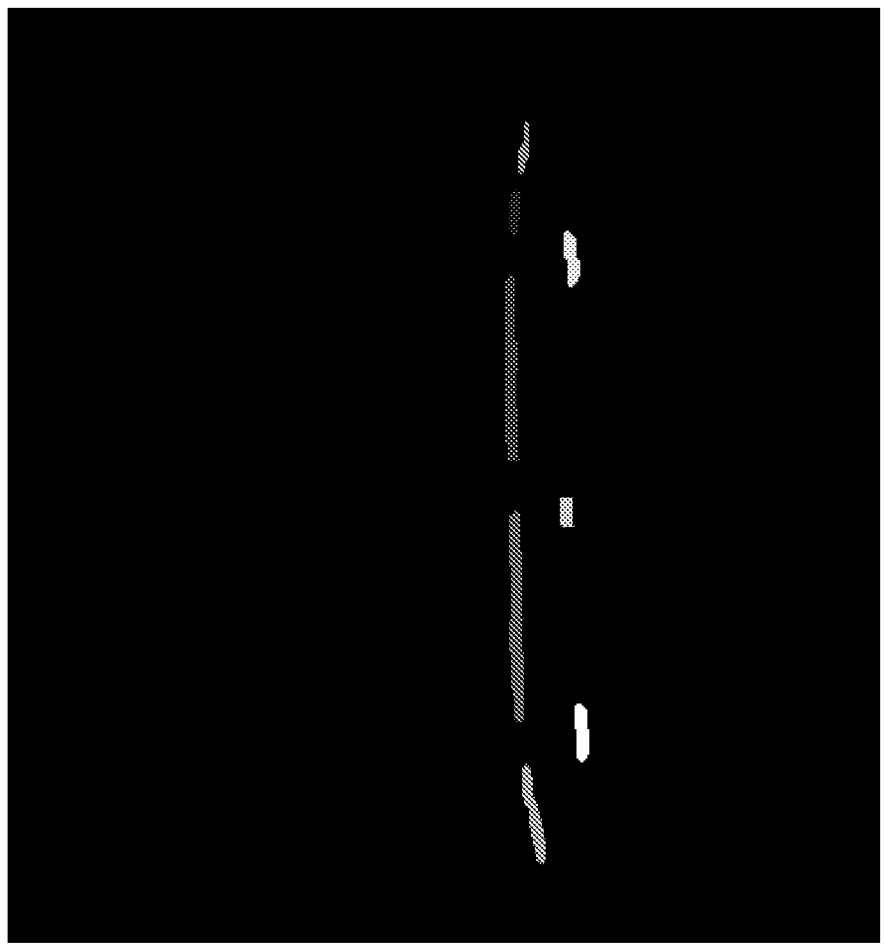
FIG. 6 is a view showing an image after labeling and noise removal.

FIG. 6 is a view showing an image after labeling and noise removal. At this stage, a linear region showing a light image of the connecting surface and an isolation region showing a light image of the bottom surface of the groove are left.

[Step A3] Extraction of Linear Region

Figure 7:
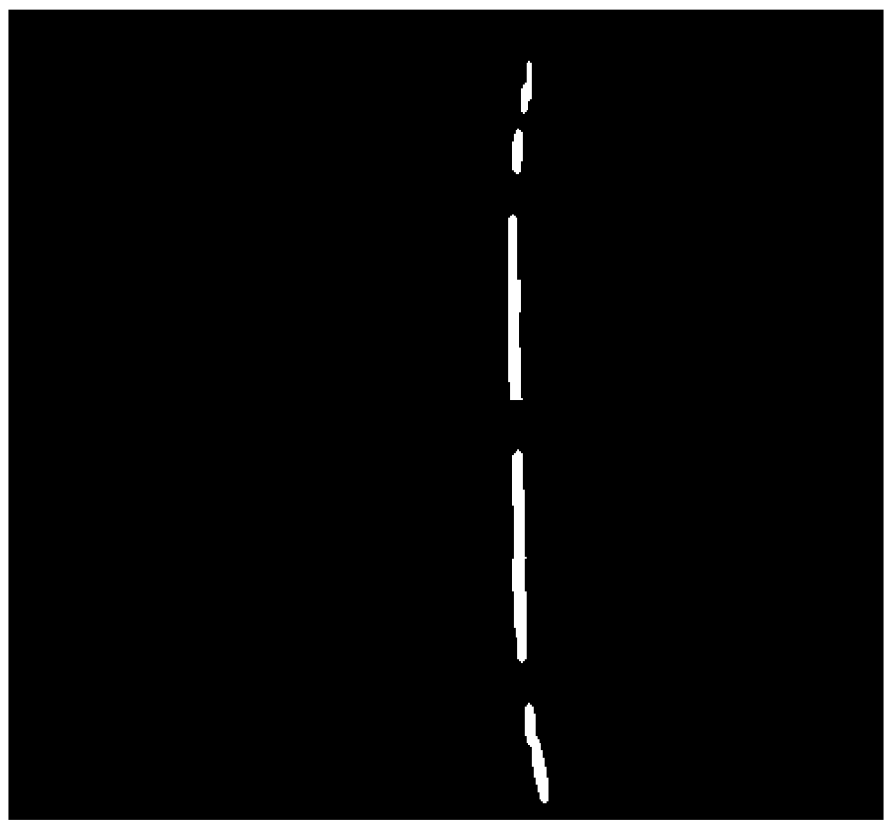
FIG. 7 is a view showing an image of an extracted linear region.

As shown in FIG. 6, the isolation region is linear with a shorter length compared to the linear region, and is almost in parallel to the linear region which is the light image of the connecting surface. Then, Hough transform is performed using all light images of the linear regions and the isolation regions to detect straight lines. Since a higher-order straight line among the straight lines detected by the Hough transform has an extremely high possibility of passing through the linear region, k higher-order straight lines (for example, k=2) are adopted, and the label through which any of the k straight lines passes is left with other labels removed, thus making it possible to remove the isolation regions. FIG. 7 is a view showing an image of an extracted linear region. A light image in which isolation regions are removed and only linear regions are left is obtained.

<Step S2> Removal of Eccentricity Component

The image obtained by extraction of the slit light image by Step S1 is a binary image, and in a binary image $f_{i,j}$, f=0 for a black pixel of a background and f=1 for a white pixel showing a light image. Here, i and j show a coordinate value in a two-dimensional image, respectively.

In order to eliminate an eccentricity component, first, the displacement of an average X coordinate value of the linear region in each frame is created as waveform data. The average X coordinate value $X_n$ of each frame becomes an average value of X coordinates of all extracted pixels as shown in the following formula (3).

[Math. 2]

$$x_n = \frac{1}{S_n} \sum g, \quad (3)$$
$$g = i$$
when
$$f_{ij} = 1$$

Here, n indicates a frame number and $S_n$ shows an area of the extracted linear region in each frame (pixel number of pixel where f=1). In addition, one which is an exponentiation of 2 is used for the number of the entire frames. In the formula (3), the x coordinate of a position of center of gravity of the linear region is calculated.

By plotting with an abscissa axis as the number of frames and an ordinate axis as the average X coordinate value, waveform data is obtained. Fourier transform is performed for the obtained waveform data to obtain a frequency spectrum. A high-frequency component is cut by a lowpass filter for the obtained frequency spectrum. By cutting the high-frequency component, only an influence of the eccentricity component is left in the frequency spectrum.

Inverse Fourier transform is performed for the frequency spectrum obtained by cutting the high-frequency component, and an average X coordinate value $X_n'$ after the high-frequency cutting is obtained. Based on the following formula (4), difference between the average coordinate value after the high-frequency cutting and the average coordinate value before the high-frequency cutting is calculated to obtain an eccentricity component $d_n$.

[Math. 3]

$$d_n = x_n' - x_n \quad (4)$$

Though various methods are considered as a method for eliminating the obtained eccentricity component, it is possible to eliminate the eccentricity component, for example, by performing parallel movement only by $d_n$ pixels for the shot image.

<Step S3> Calculation of Feature Quantity

As to the feature quantity, one frame is divided into a plurality of blocks to obtain an average X coordinate value for each block. The block is one which is divided in a direction perpendicular to the slit, and has 10 mm width for example.

With the average value of the x coordinate in the b-th block of the n-th frame as $X_{n,b}$, this is calculated for all frames. The average X coordinate value $X_{n,b}$ can be obtained by the following formula (5).

[Math. 4]

$$X_{n,b} = \frac{1}{S_{n,b}} \sum g, \quad (5)$$
$$g = i$$
when
$$f_{ij} = 1$$

Next, an average X coordinate value $M_b$ for each block in all frames is obtained. The average X coordinate value $M_b$ is obtained by calculating an average value of all frames with respect to one block based on the following formula (6).

[Math. 5]

$$M_b = \frac{1}{N} \sum_{n=1}^{N} X_{n,b} \quad (6)$$

Here, N is a total number of frames, and the average X coordinate value $M_b$ is obtained by dividing the sum of the average X coordinate values of one block in all frames by the total number of frames. N may be selected appropriately depending on a size or type of the tire, and, for example, when an outer circumferential length of the tire is 2000 mm, the number of frames my be 100 so that a defect is shot.

A feature quantity $F_{n,b}$ is obtained as a difference value between the average X coordinate value $X_{n,b}$ and the average X coordinate value $M_b$ for each block as shown in the following formula (7).

[Math. 6]

$$F_{n,b} = |X_{n,b} - M_b| \quad (7)$$

<Step S4> Detection of Defect

When the feature quantity $F_{n,b}$ is larger than a threshold α, it is possible to detect that a defect is shot in an image of b-th block of the n-th frame. Since the frame shows a position of a circumferential direction and the block shows a position of a width direction, when the frame and block in which the defect is shot are identified, the actual position of the defect is found.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

1: Tire
2: Rotational table
3: Slit light source
4: Area camera

The invention claimed is:

1. A tire defect detection method for detecting a convex defect in a contact area of a tire comprising tread pattern elements, comprising:
a shooting step of successively shooting two-dimensional images of an area of the tire including a region irradiated with slit light by irradiating a tire tread with the slit light so that a longitudinal direction thereof becomes parallel to a width direction of the tire, while rotating the tire about a predetermined axis;
an extraction step of removing, from among light images of the slit light appearing in respective shot two-dimensional images, a light image other than linear light images which are light images of the contact area of the tire and extracting the linear light images;
an eliminating step of eliminating an influence of displacement of the contact area resulting from the rotation of the tire, from the two-dimensional images including the extracted linear light images;

a calculation step of calculating a difference between a position of the linear light image in each of the two-dimensional images from which the influence of displacement is eliminated and an average position of linear light images in all two-dimensional images from which the influence of displacement is eliminated as a feature quantity for each of the two-dimensional images; and a detection step of comparing a calculated feature quantity for each of the two-dimensional images and a predetermined threshold, and in a case where the feature quantity is larger than the predetermined threshold, determining that the tire has some defect.

2. The tire defect detection method according to claim 1, wherein in the eliminating step, a position of center of gravity of the extracted linear light image is calculated for each of the two-dimensional images including the extracted linear light image, Fourier transform is performed for a change between calculated positions of center of gravity as waveform data, inverse Fourier transform is performed for a frequency spectrum which is obtained by eliminating a high-frequency component from the frequency spectrum obtained by Fourier transform, a position of center of gravity after transform that is a position of center of gravity after inverse Fourier transform is obtained, and a difference between the position of center of gravity and the position of center of gravity after transform is defined as an influence of displacement of the contact area.

3. The tire defect detection method according to claim 1, wherein in the calculation step, the two-dimensional image from which the influence of displacement is eliminated is divided into a plurality of blocks in parallel to a circumferential direction of the tire and a feature quantity for respective divided blocks is calculated.

4. The tire defect detection method according to claim 2, wherein in the calculation step, the two-dimensional image from which the influence of displacement is eliminated is divided into a plurality of blocks in parallel to a circumferential direction of the tire and a feature quantity for respective divided blocks is calculated.

* * * * *